United States Patent [19]

Belly et al.

[11] Patent Number: 4,556,636

[45] Date of Patent: Dec. 3, 1985

[54] COMPOSITION, ANALYTICAL ELEMENT AND METHOD FOR THE DETECTION OF BACTERIA

[75] Inventors: Robert T. Belly, Webster; Laurie J. Clements, Rochester, both of N.Y.

[73] Assignee: Eastman Kodak Company, Rochester, N.Y.

[21] Appl. No.: 502,815

[22] Filed: Jun. 9, 1983

[51] Int. Cl.⁴ .............................................. C12Q 1/04
[52] U.S. Cl. ........................................ 435/34; 435/29
[58] Field of Search ............... 544/345; 546/195, 272; 548/152, 427, 440; 435/4, 28, 29, 34

[56] References Cited

U.S. PATENT DOCUMENTS

| | | | |
|---|---|---|---|
| 3,415,717 | 12/1968 | Avakisa | 435/37 |
| 3,496,066 | 2/1970 | Berger et al. | 435/35 |
| 3,501,312 | 3/1970 | Mee et al. | 430/579 |
| 3,505,070 | 4/1970 | Litzerman et al. | 430/567 |
| 3,621,016 | 11/1971 | Berger et al. | 546/125 |
| 3,712,853 | 1/1973 | Rittersdorf et al. | 435/37 |
| 3,992,158 | 11/1976 | Przybylowicz | 435/28 |
| 4,232,121 | 11/1980 | Gilman, Jr. et al. | 435/32 |
| 4,336,337 | 6/1982 | Wallis et al. | 435/292 |
| 4,418,037 | 11/1983 | Katsuyama et al. | 436/135 |

OTHER PUBLICATIONS

"A Simple Semi-Quantitative Diagnostic Screening Method for Presumptive Bacteriuria", Pfizer, Diagnostics Div., N.Y., 1974.
"Test for Nitrite with Miniaturized Culture Tests for Total Bacterial Gram-Negative Bacterial Counts in Urine", Ames Co. (Division of Miles Lab.), Elkhart, IN, 1976.
Montgomerie et al, *Am. J. Med. Sci.*, 251:94–97, 1966.

*Primary Examiner*—Robert J. Warden
*Assistant Examiner*—William J. Herald
*Attorney, Agent, or Firm*—J. Lanny Tucker

[57] ABSTRACT

A composition, an analytical element and a method for the detection of bacteria in specimen samples, e.g. biological fluids, are disclosed. The composition optionally, but preferably, comprises a metabolizable substrate (e.g. glucose) and a benzindole dye which undergoes a detectable color change when incubated in admixture with a bacterial microorganism. Useful dyes include particular benz[cd]indole, benz[e]indole and benz[g]indole compounds. The described analytical element contains this composition, preferably, in a spreading zone. Detection of bacteria can be accomplished by bringing the composition or element into contact with a specimen sample. This invention is particularly useful in detection of significant bacteriuria.

25 Claims, No Drawings

COMPOSITION, ANALYTICAL ELEMENT AND METHOD FOR THE DETECTION OF BACTERIA

FIELD OF THE INVENTION

The present invention relates to the detection of bacteria in specimen samples with benzindole dyes. More specifically, it relates to a composition, an analytical element and a method using same for detection of bacteria in biological fluids, e.g. urine.

BACKGROUND OF THE INVENTION

For the rapid and effective diagnosis and treatment of infectious diseases, it is desirable to be able to detect the bacteria causing the disease as rapidly as possible. Infections of the urinary tract are among the most common bacterial diseases, second in frequency only to infections of the respiratory tract. In fact, in many hospitals, urinary tract infections are the most common form of nosocomial infections, often following the use of indwelling catheters and various surgical procedures. Most urinary tract infections (UTI) result from ascending infection by microorganisms introduced through the urethra and vary in severity from an unsuspected infection to a condition of severe systemic disease. Such infections are usually associated with bacterial counts of 100,000 ($10^5$) or more organisms per mL of urine, a condition referred to as significant bacteriuria. Under normal conditions, urine is sterile, although contamination from the external genitalia may contribute up to 1,000 ($10^3$) organisms per mL in properly collected and transported specimens.

Significant bacteriuria may be present in a number of pathological conditions involving microbial invasion of any of the tissues of the urinary tract, or may result from simple bacterial multiplication in the urine without tissue invasion. The infection may involve a single site such as the urethra, prostate, bladder, or kidney, although frequently it involves more than one site. Infection restricted to the urine may present itself as asymptomatic bacteriuria, i.e., a condition which manifests no overt signs or symptoms of infection. Early treatment of this condition can prevent the development of more serious conditions, e.g., pyelonephritis (inflammation of the kidney and the renal pelvis). The rapid detection of bacteria by a reliable method would therefore facilitate an early and specific diagnosis.

Further, in order to insure that a prescribed antibiotic is in fact effective in treating an infection, repeated tests during therapy are required. The need for simple, rapid bacteriuria tests is thus clear. Moreover, in view of the frequent unsuspected asymptomatic occurrences of UTI among children, pregnant women, diabetics and geriatric populations, diagnosis of which may require collection and testing of several specimens, bacteriuria tests must be sufficiently simple and economical to permit routine performance. Again, this illustrates the need for a rapid and inexpensive bacteriuria detection method.

Current laboratory methods based on culturing microorganisms, e.g., the calibrated loop-direct streak method, require significant incubation periods (18-24 hours) before results can be determined. These laboratory methods are also time-consuming to perform and require considerable clinical training and facilities.

Known methods for the relatively rapid detection of bacteriuria include:

1. Uroscreen TM (triphenyltetrazolium chloride) is described in a brochure entitled "A Simple Semi-quantitative Diagnostic Screening Method for Presumptive Bacteriuria" published by Pfizer, Diagnostics Division, NY, 1974. Uroscreen TM utilizes a dry, buffered tetrazolium reagent (colorless, soluble 2,3,5-triphenyltetrazolium chloride). In the presence of significant bacteriuria, Uroscreen TM will be reduced by the metabolizing bacteria within 4 hours to a pink-red, insoluble precipitate of triphenylformazan. This method has several disadvantages: it may not be accurate because bloody urine includes deposits resembling the pink-red precipitate of a positive test; and highly colored urine (caused by concentration, bilirubin, or drug ingestion) may obscure the results. The accuracy of this test in detecting significant bacteriuria has been reported to be from about 60 to about 90%.

2. Microstix TM -3 Reagent Strips for Urinalysis are described in a brochure entitled "Test for Nitrite with Miniaturized Culture Tests for Total Bacterial Gram-Neg Bacterial Counts in Urine," published by Ames Co. (Division of Miles Laboratories, Inc.), Elkhart, IN, 1976. Microstix TM -3 is a firm, plastic strip to which three separate reagent areas are affixed, i.e. a chemical test area for the immediate recognition of nitrite in urine and two culture areas for semi-quantitation of bacterial population. The nitrite test, based on a modification of the known Griess nitrite reaction, depends upon the conversion of nitrate (derived from dietary metabolites) to nitrite by the action of certain species of bacteria in the urine. However, a negative result from this test does not provide proof that the urine is sterile. This can be a problem, particularly if there are clinical signs or symptoms to indicate a bacterial infection. Also, blood, Pyridium TM, bilirubin, methylene blue, and other interferents in the sample may obscure the test results. This method also has several disadvantages inherent to nitrite tests: it must be performed on first-morning specimens for optimum accuracy; it may give false negative results on specimens collected from patients on low-nitrate diets; it can be blocked or interfered with by phenzapyridine hydrochloride or any drug to which the bacteria are susceptible; it requires a large bacterial population for positive results; and it will not detect microorganisms which do not reduce nitrate to nitrite.

3. Montgomerie, J. Z., Kalmanson, G. M., and Guze, L. B. describe the catalase test in "The Use of the Catalase Test to Detect Significant Bacteriuria," *Am. J. Med. Sci.*, 251:94-97, 1966. The catalase test is based on rapid gas production resulting from urea reacting with hydrogen peroxide. This reaction is catalyzed by catalase available from bacteria in the specimen sample. The method has several drawbacks for detecting bacteriuria, however: microorganisms which lack catalase, or those containing low levels of catalase may provide false negative results; and reducing chemicals present in urine capable of reacting with hydrogen peroxide may interfere with the test.

Other diagnostic agents for detecting bacteria in biological and other fluids are described in U.S. Pat. No. 3,496,066 (issued Feb. 17, 1970 to Berger et al) and U.S. Pat. No. 3,621,016 (issued Nov. 16, 1971 to Berger et al). Such agents are metabolized by bacteria present in the sample specimen to produce detectable products.

Hence, there is a need for a simple, reliable and inexpensive procedure for rapid detection of bacteria, and particularly significant bacteriuria, which procedure avoids the problems presented with known procedures.

SUMMARY OF THE INVENTION

The present invention provides a composition, an analytical element and a method for the detection of bacteria in specimen samples, e.g. biological fluids, by the use of certain benzindole dyes. This invention overcomes the above-described problems inherent with known detection procedures.

In particular, among the advantages derived from the present invention are: (1) rapid detection of bacteria, i.e., generally 60 minutes or less; (2) minimized color interference due to blood or other substances that may be present in the sample being evaluated (the preferred dyes, the benz[cd]indoles, absorb maximally in the 620 nm region and reduce in the 400–450 nm region); and (3) suitability for use in both solution and dry chemistry formats.

In accordance with this invention, a composition for the detection of bacteria comprises a metabolizable substrate and a benzindole dye which undergoes a detectable color change when incubated in admixture with a bacterial microorganism. Such dye is a benz[c-d]indole, benz[e]indole or benz[g]indole dye.

This invention also provides an element for detecting bacteria. This element comprises a support and a benzindole dye which undergoes a detectable color change when incubated in admixture with a bacterial microorganism. The dye is benz[cd]indole, benz[e]indole or benz[g]indole dye.

This invention further provides a method for the detection of bacteria comprising bringing a specimen sample for analysis into contact with a benzindole dye which undergoes a detectable color change when incubated in admixture with a bacterial microoganism. Such dye is a benz[cd]indole, benz[e]indole or benz[g]indole dye. The method can be practiced in either solution or dry analytical format.

DETAILED DESCRIPTION OF THE INVENTION

The present invention relates to the detection of bacteria, and particularly significant bacteriuria (i.e. at least about $10^5$ microorganisms per mL), in specimen samples, such as liquids. Although any specimen sample suspected of having bacteria therein (e.g. food, tissue, ground water, cooling water, pharmaceutical products, sewage, etc.) can be assayed, the invention is particularly useful for bacterial detection in aqueous liquids, such as human and animal biological fluids (e.g. urine, spinal fluid, blood and the like as well as stool secretions) and suspensions of human or animal tissue. The preferred biological fluid used in practicing this invention is human urine (diluted or undiluted).

The benzindole dyes useful in the practice of this invention are capable of undergoing a detectable color change when incubated in admixture with a bacterial microoganism, e.g. *Escherichia coli*. Generally, such dyes are selected from the group consisting of benz[c-d]indole dyes, benz[e]indole dyes and benz[g]indole dyes. However, it should be understood that not all benzindole dyes are operable for this purpose. The determination of whether a given benzindole dye is operable and within the scope of the present invention can be made by a simple test comprising incubating the dye in admixture with an aqueous suspension of a particular microorganism at 37° C. and observing whether the dye is reduced by the microorganism to produce a detectable change in the visible color of the dye. Generally, a visible color change occurs in the 400 to 700 nm range of the electromagnetic spectrum. More than one dye can be used in the compositions of this invention, although preferably, only one dye is used.

Benzindole dyes particularly useful in the practice of this invention undergo the described color change and have a structural formula selected from the group consisting of:

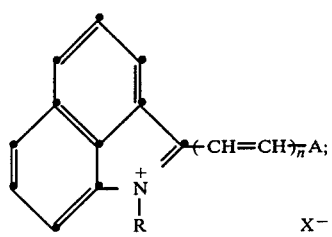

I.

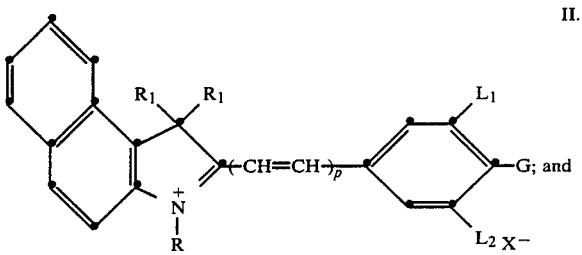

II.

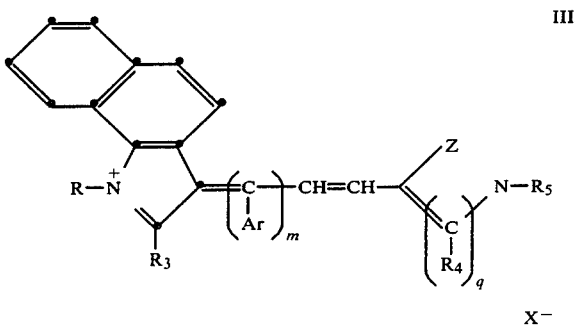

III.

wherein:

A is selected from the group consisting of:

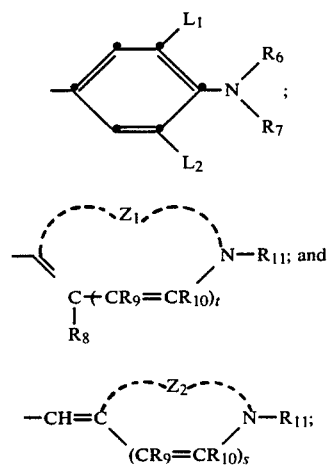

R, $R_4$, $R_5$ and $R_{11}$ are independently hydrogen, alkyl, aryl, alkaryl, aralkyl or cycloalkyl;

$R_1$ and $R_2$ are independently hydrogen or lower alkyl, or taken together complete a 5- to 6-membered carbocyclic ring;

$R_3$ is aryl;

$R_6$ and $R_7$ are independently hydrogen, alkyl, cycloalkyl or aryl, or taken together complete a 4- to 20-membered heterocyclic group;

$R_8$, $R_9$ and $R_{10}$ are independently hydrogen, halo, alkyl, aryl, alkaryl, aralkyl or cycloalkyl;

G is —$OR_{12}$ or

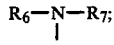

$R_{12}$ is lower alkyl;

$L_1$ and $L_2$ are independently hydrogen, or $L_1$ represents atoms taken with $R_6$ to complete a 5- or 6-membered ring or $L_2$ represents atoms taken with $R_7$ to each complete a 5- or 6-membered ring;

Ar is aryl;

m and q are independently 0 or 1;

n is 0, 1, 2 or 3;

p is 1, 2 or 3, except when G is

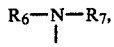

p is 2 or 3;

t is 0, 1 or 2;

s is 0, 1 or 2, except when n is 1, s is 1 or 2;

Z represents the carbon, selenium, sulfur or nitrogen atoms needed to complete a heterocyclic group;

$Z_1$ and $Z_2$ independently represent a single bond or the carbon, selenium, sulfur or nitrogen atoms needed to complete a heterocyclic group; and $X^-$ is a monovalent anion.

In the above formulae I, II and III, the dyes can contain one or more other non-interfering substituents which will not adversely interfere with the dye's solubility characteristics and capability to change color in the presence of bacteria (i.e. capability of being reduced by the bacteria). Any of the substituents described below, i.e. R, $R_1$, $R_2$, $R_3$, G, A, etc. can likewise have one or more of such non-interfering substituents attached thereto, as is known by a worker skilled in dye chemistry.

In the above formulae I, II and III, R, $R_4$, $R_5$ and $R_{11}$ can be hydrogen, alkyl (substituted or unsubstituted), aryl (substituted or unsubstituted), alkaryl, aralkyl or cycloalkyl. Where any of these groups is alkyl, the alkyl chain can be straight or branched and preferably, but not necessarily, has from 1 to 12 carbon atoms (e.g. methyl, ethyl, n-propyl, n-butyl, n-heptyl, n-nonyl, n-undecyl, n-dodecyl, etc. and isomers thereof). More preferably, each of these groups is hydrogen or a lower alkyl having from 1 to 4 carbon atoms (e.g. methyl, n-propyl, isopropyl, t-butyl, etc.) Where R, $R_4$, $R_5$ or $R_{11}$ is substituted, it preferably contains halo, hydroxy, (alkoxycarbonylalkyl)carbamoyloxy.

Where R, $R_4$, $R_5$ or $R_{11}$ is aryl, it preferably, but not necessarily, has from 6 to 20 carbon atoms forming ring systems which are more preferably phenyl or naphthyl, and which can, if desired, have one or more non-interfering substituents attached thereto as described hereinabove (e.g. halo, hydroxy, alkyl, oxyalkyl, etc.).

When R, $R_4$, $R_5$ or $R_{11}$ is alkaryl or aralkyl, it is also preferred, but not necessary, that it have from 7 to 20 carbon atoms (e.g. benzyl, ethylenephenyl, 2-ethylenephenyl, etc.). Preferably, it is benzyl. Also, any of these groups can be cycloalkyl having, preferably from about 6 to about 20 carbon atoms (e.g. cyclohexyl, cycloheptyl, etc.). Preferably, the cycloalkyl group is cyclohexyl.

$R_1$ and $R_2$ in formula II above are independently hydrogen or lower alkyl (preferably of from 1 to 4 carbon atoms as described for $R_{12}$ below), or taken together complete a 5- to 6-membered carbocyclic ring (e.g. cyclopentyl, cyclohexyl, phenyl, etc.). It is preferred that $R_1$ and $R_2$ be identically hydrogen or lower alkyl. Where each is lower alkyl, it is particularly preferred that each is methyl.

In formula III hereinabove, $R_3$ is aryl as defined for R, $R_4$, $R_5$ or $R_{11}$. Preferably, $R_3$ is phenyl (unsubstituted or substituted as noted hereinabove).

G in formula II hereinabove can be —$OR_{12}$ wherein $R_{12}$ is lower alkyl of from 1 to 4 carbon atoms (e.g. methyl, chloromethyl, ethyl, isopropyl, t-butyl, etc.). Alternatively and preferably, G is

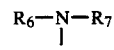

wherein $R_6$ and $R_7$ (here as well as in the group A) are independently alkyl or aryl as described hereinabove for R, $R_4$, $R_5$ and $R_{11}$, or taken together, $R_6$ and $R_7$ can complete a 4- to 20-membered heterocyclic group. Preferably, $R_6$ and $R_7$ are independently lower alkyl of from 1 to 4 carbon atoms as described for $R_{12}$ hereinabove. Most preferably, both $R_6$ and $R_7$ are methyl.

$R_8$, $R_9$ and $R_{10}$ are independently hydrogen, halo (fluoro, chloro, bromo and iodo), alkyl, aryl, alkaryl, aralkyl or cycloalkyl which are defined similar to R, $R_4$, $R_5$ and $R_{11}$ hereinabove.

$L_1$ and $L_2$ in formulae I and II are independently hydrogen, or $L_1$ represents atoms taken with $R_6$ to complete a 5- or 6-membered ring and $L_2$ represents atoms taken with $R_7$ to each complete a 5- or 6-membered ring. Those rings could be a part of a larger ring having from 10 to 12 members. Preferably, each of $L_1$ and $L_2$ is hydrogen.

Ar in formula III above is aryl preferably, but not necessarily, of from 6 to 12 carbon atoms as described above for $R_3$. More preferably, Ar is phenyl or naphthyl.

Z in formula III preferably represents the carbon, selenium, sulfur or nitrogen atoms needed to complete a 4- to 20-membered heterocyclic group, such as nitrobenzothiazole, nitrobenzoxazole, nitrobenzoselenazole, nitro-3H-indole, imidazo[4,5-b]quinoxaline, and pyrrolo[2,3-b]pyridine.

$Z_1$ and $Z_2$ independently represent either a single bond (e.g. between a nitrogen and a carbon atom), or the carbon, selenium, sulfur or nitrogen atoms needed to complete a heterocyclic group as defined for Z.

In formula I above A is preferably

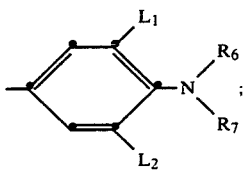

and n is at least 1.

In formula II above, p is preferably 2 or 3.

$X^-$ in all of the formulae represents a monovalent anion, which can be, for example, p-toluenesulfonate; halide, such as iodide, chloride, or bromide; acetate; or perchlorate.

The benzindole ring systems in all of the above formulae, I, II, and III, can be substituted with an appropriate electron-withdrawing or electron-donating group, such as alkyl, aryl, alkoxy, cyano, nitro, halo or others known to those skilled in the art which will not interfere with the solubility characteristics or other desirable properties of the dye.

As would be recognized by a worker skilled in the art, the dyes represented by formula III can exist in several tautomeric forms, depending upon what m and q are. The structure shown hereinabove clearly shows the dye structure when both m and q are 1. If both m and q are 0, the dye structure is represented by the formula:

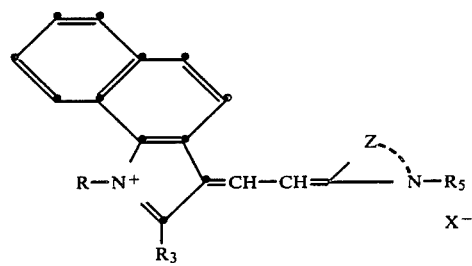

IIIa.

wherein R, $R_3$, $R_5$, Z and $X^-$ are as defined hereinabove. If m is 1 and q is 0, the dye structure is represented by the formula:

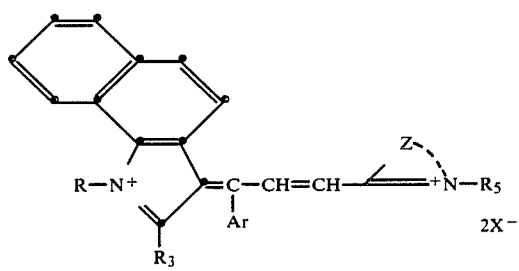

IIIb.

wherein R, $R_3$, $R_5$, Z and $X^-$ are as defined hereinabove. If m is 0 and q is 1, the dye structure is represented by the formula:

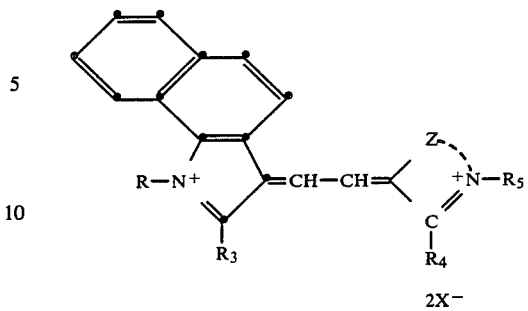

IIIc.

wherein R, $R_3$, $R_4$, $R_5$, Z and $X^-$ are as defined hereinabove. In formulae IIIb and IIIc, the dye contains two positive charges and, hence, two balancing monovalent anions (which can be the same or different).

The dyes employed in the practice of the present invention are known in the art and many of them are commercially available, for example, from Eastman Organic Chemicals, Rochester, N.Y. Some of these dyes are described in published references including, for example, U.S. Pat. No. 3,501,312 (issued Mar. 17, 1970 to Mee et al); and U.S. Pat. No. 3,505,070 (issued Apr. 7, 1970 to Litzerman et al). Some of the dyes are advantageously water soluble. However, in the practice of this invention as described in detail in the Examples hereinbelow, all dyes were prepared and stored at $10^{-3}$ molar methanolic solutions although depending upon the extinction coefficient of the dye, it can be used in a concentration up to about $10^{-1}M$, and preferably in a range of from about $10^{-7}$ to about $10^{-2}M$ in the compositions of this invention. To minimize the possible effects of light, all the work reported in the Examples were performed under yellow lights and, unless otherwise specified, all test tubes were incubated in the dark. Exemplary dyes useful in the practice of this invention are listed in Table I hereinbelow. A preferred dye is:

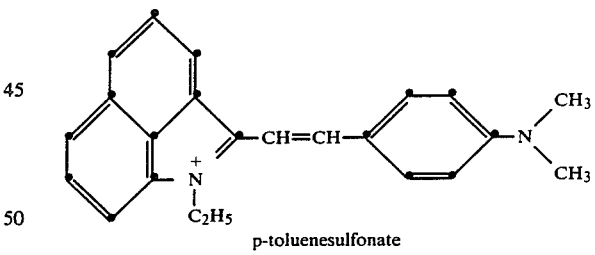

p-toluenesulfonate

Although it is not necessary to include a metabolizable substrate in the elements and methods of this invention, use of such substrates is preferred in order to stimulate bacterial metabolism and consequently, to facilitate detection. Any conventional metabolizable substrate can be used as is known to one skilled in the art. Other terms for metabolizable substrate are "energy source" and "carbon source", the latter term indicating that the compound is a source of metabolizable carbon for the bacteria. Suitable substrates are described in U.S. Pat. No. 4,035,237 (issued July 12, 1977 to Masurekar et al) and include sugars, e.g. glucose, fructose, sucrose, lactose, maltose, raffinose, etc.; starch; salts of carboxylic acids, e.g. lactate, citrate, malate, succinate, etc.; glycols, e.g. glycerol, sorbitol, dulcitol, mannitol, etc.; and others known to a skilled worker in the microbiology art. The concentration of the metabolizable substrate generally ranges from about 0.01 to about 1 percent, by weight, of total composition weight when the composition is used in solution assay procedures.

The method and composition of this invention are adaptable to both solution and dry element assays. Thus, an aqueous or alcoholic solution containing the described benzindole dye and, preferably, one or more metabolizable substrates is prepared and bacteria are detected by contacting a sample of the specimen to be tested (e.g. a urine specimen) with a predetermined volume of the dye solution. Alternatively, the metabolizable substrate can be present in the test sample prior to addition of dye.

In solution assay, generally the dye solution is added to the specimen sample to be tested which is in a suitable container (e.g. test tube, petrie dish beaker, other suitable laboratory container). The resulting solution is gently mixed and incubated for a relatively short time (i.e. less than about 60 minutes) at 37° C. The color of the dye in the incubated solution is then observed (over a time up to several hours if necessary) and compared to a control solution similarly prepared and handled but without any bacteria therein. If the incubated solution contains microorganisms, the dye therein will exhibit a visible color change, i.e. a change from one color to another, from a color to colorless, or from colorless to a color.

Alternatively, the benzindole dyes can be incorporated into a porous lamina, i.e., a matrix or support of absorbent material, such as filter paper strips, by impregnation or otherwise, to yield an analytical element suitable for the detection of bacteria in a specimen sample deposited thereon.

In addition, the method is used to particular advantage when carried out in an analytical element having a support and a spreading zone of the type described in U.S. Pat. No. 3,992,158 (issued Nov. 16, 1976 to Przybylowicz et al) or U.S. Pat. No. 4,258,001 (issued Mar. 24, 1981 to Pierce et al), the disclosures of which are incorporated herein by reference. The presence or absence of bacteria is then determined by contacting (e.g. spotting) the element with the specimen sample suspected of containing bacteria. The specimen sample here is usually a suspension of bacteria in a liquid (e.g. an aqueous liquid). The presence of bacteria in significant numbers will then cause a visible color change in the benzindole dye located in the element.

The analytical element of this invention generally has a reagent zone containing the benzindole dye, and optionally, a metabolizable substrate described herein. This zone can be self-supporting, or alternatively, the element can also comprise a support. Where a single zone is used, it is sometimes called a spreading/reagent zone. The element preferably includes a support and a plurality (at least a first and second) of zones. Preferably, the first zone is adjacent the support. These zones are in fluid contact with each other, meaning that fluids can pass between superposed regions of adjacent zones. Stated in another manner, fluid contact refers to the ability to transport components of a fluid between the zones in fluid contact. Preferably, the zones are separate coated layers, although one or more zones can be in a single layer of an element. Suitable dry element formats are known in the art and described, for example, in U.S. Pat. No. 3,992,158 noted hereinabove; as well as in U.S. Pat. No. 4,042,335 (issued Aug. 16, 1977 to Clément); U.S. Pat. No. 4,144,306 (issued Mar. 13, 1979 to Figueras); U.S. Pat. No. 4,132,528 (issued Jan. 2, 1979 to Eikenberry et al); U.S. Pat. No. 4,050,898 (issued Sept. 27, 1977 to Goffe et al); and U.S. Pat. No. Re. 30,267 (reissued May 6, 1980 to Bruschi).

The support for the element can be composed of any dimensionally stable material (e.g. poly(ethylene terephthalate)) and is preferably transparent.

Other materials and elements which are adapted for use in the practice of this invention are described, for example, in U.S. Pat. Nos. 3,092,465, 3,418,099, 3,418,083, 2,893,843, 2,893,844, 2,912,309, 3,008,879, 3,802,842, 3,798,064, 3,298,739, 3,915,647, 3,917,453, 3,993,594, 3,936,357, 4,270,920, 4,248,829, 4,255,384, 4,256,693, U.K. Pat. No. 2,052,057 and *Research Disclosure*, Vol. 146, June 1976, Item 14638.

In a preferred embodiment of this invention, the element includes a support having thereon and in fluid contact, reagent and spreading zones. The benzindole dye described herein is preferably in the reagent zone which is a reagent layer adjacent the support. The spreading zone is a spreading layer preferably adjacent the reagent layer, although there can be one or more intervening layers. Preferably, this speading layer comprises beads composed of poly(vinyltoluene-co-p-t-butylstyrene-co-methacrylic acid) and a suitable binder, if desired.

In the elements of this invention, the amount of the benzindole dye can be varied widely, but it is present generally in a coverage of up to about 5 $g/m^2$ and preferably, from about 0.05 to about 2 $g/m^2$. Similarly, when present, the amount of the metabolizable substrate can be widely varied, but it is generally present in a coverage of from about $10^{-3}$ to about 1 $g/m^2$ and preferably, from about 0.01 to about 0.5 $g/m^2$. The substrate can be present in any zone (or layer) of the element, but it is preferably in the same zone (or layer) as the benzindole dye.

One or more of the zones of the elements of this invention can contain a variety of other desirable, but optional, components, including buffers, surfactants, and binders (typically hydrophilic) as is known in the art.

Further details of the elements, particularly suitable components of the spreading zones, are given in U.S. Pat. Nos. 3,992,158 and 4,258,001 noted hereinabove; and U.K. Patent Application No. 2,052,057 (published Jan. 21, 1981). The spreading zones, for example, can be composed of either fibrous or non-fibrous materials, or both.

Exemplary elements are illustrated hereinbelow in Examples 5 and 6.

The following examples are provided to illustrate the practice of this invention. In these examples, *Enterobacter cloacae* (ATCC 23355), *Escherichia coli* (ATCC 25922), *Klebsiella pneumoniae* (ATCC 13883), *Proteus vulgaris* (ATCC 13315), *Pseudomonas aeruginosa* (ATCC 27853), *Serratia marcescens* (ATCC 8100), *Staphylococcus aureus* (ATCC 25923), *Staphylococcus epidermidis* (ATCC 12228), and *Streptococcus pyogenes* (ATCC 19615) were obtained from Difco Laboratories, Detroit, MI.

All cultures were routinely grown in 125 mL flasks containing 50 mL of commercially-available brain-heart infusion medium and incubated at 37° C. prior to use.

Where cell suspensions were used, a 24-hour culture was centrifuged at 5000 xg for 10 minutes. The resulting pellet was washed twice in 0.05M potassium phosphate buffer (pH 7.0), and resuspended (1:4 aqueous dilution), to give a final optical density of 2.0, as measured on a Bausch and Lomb Spectronic ™ 20 spectrophotometer at 620 nm.

To each 5 mL of cell suspension, 0.1 mL of 10% w/v glucose was added.

The urine samples employed in the examples were obtained from a local hospital. To minimize microbial contamination and growth in the samples, two 5 mL urine samples from the same source were placed in separate transport tubes supplied in B-D Urine Culture Kits obtained from Becton Dickinson and Company, Rutherford, NJ. These tubes contained a preservative, 0.5 mL boric acid-glycerol-sodium formate, which maintains a stable bacterial population. The tubes were refrigerated and all samples were used within 24 hours.

The urine samples were analyzed according to the following procedure: the contents of two 5 mL urine samples were combined in a 15 mL centrifuge tube and centrifuged at 10,000 xg for 10 minutes, after which the clear supernatant was discarded. The resulting pellet was resuspended in 1.5 µL of 0.05M potassium phosphate buffer (pH 7.0), and thoroughly mixed using a conventional high speed mixer. Unless otherwise specified, 25 µL of a benzindole dye solution ($10^{-3}$M dye in methanol) were added to each centrifuge tube. The contents of each tube were then gently agitated and incubated for 30 minutes at 37° C. in the dark. Preferably, a metabolizable substrate is present during this incubation. A scan of the visible spectrum of each tube was then made using a Perkin-Elmer 572 spectrophotometer. In most cases, a slit width of 1 nm and a scan speed of 120 nm/min. were used.

Control tubes containing 0.05M potassium phosphate buffer (pH 7.0) and 25 µL of benzindole dye solution were used in all studies. Where a metabolizable substrate was used, it was also included in the control tubes.

EXAMPLE 1

Color Change in Selective Benzindole Dyes in Presence of Microorganisms

Cell suspensions of a urinary tract bacteria, *E. coli* were prepared as described above. To each 5 mL of cell suspension, 0.1 mL of each dye solution containing the dyes shown in Table I hereinbelow, was added. A readily utilizable metabolizable substrate, 0.1 mL of 10% w/v glucose, was added to each resulting mixture. Control tubes without microorganisms were prepared as described above. The contents of each tube were gently mixed and incubated for 30 minutes at 37° C. in the dark. The color of the dye was noted in each sample tube containing a cell suspension and compared to the color in the corresponding control tube. The results, summarized in Table I, show benzindole dyes that are useful in the practice of the present invention as well as dyes that are not as useful. All of the dyes which gave a color change (I, II, IV, V, VII–XII, XXIII–XXVII and XXXI–XXXV) are useful in the practice of this invention, although some of them are particularly superior, notably those within formulae I, II and III described herein. Dye I is most preferred.

TABLE I

| Microbially Catalyzed Color Changes with Benzindole Dyes | |
|---|---|
| Dye | Visible Color Change |
| I. 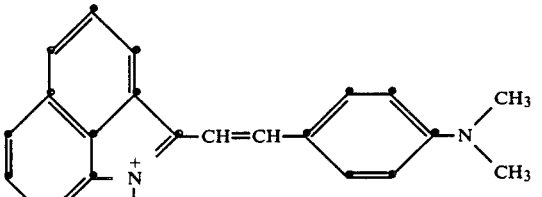 | Blue to yellow |
| II. 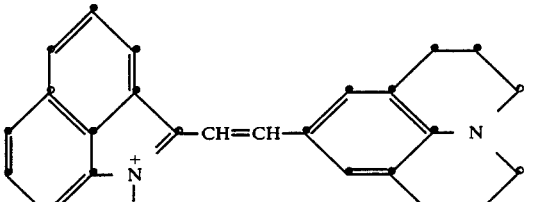 | Blue to yellow |
| III. 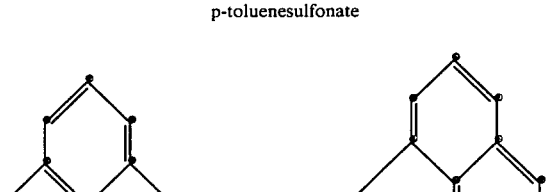 | No change |

TABLE I-continued

Microbially Catalyzed Color Changes with Benzindole Dyes

| Dye | Visible Color Change |
|---|---|
| IV. [benzindole dye structure with -CH=CH-CH=CH-CH= pentamethine bridge linking two N-ethyl benzindolium groups; I⁻ counterion] | Blue to green |
| V. [benzindole dye structure with -CH=CH-CH=CH-CH=CH-CH= heptamethine bridge linking two N-ethyl benzindolium groups; I⁻ counterion] | Blue-green to green |
| VI. [N-ethyl benzindolium linked via -CH=CH-CH= to a 6-nitro-3-ethylbenzothiazole; p-toluenesulfonate] | No change |
| VII. [N-ethyl benzindolium linked via -CH=CH-CH= to an imidazoline bearing two allyl (CH₂-CH=CH₂) N-substituents and a dimethylphenyl-N group; p-toluenesulfonate] | Blue to green |

TABLE I-continued

Microbially Catalyzed Color Changes with Benzindole Dyes

| Dye | Visible Color Change |
|---|---|
| VIII. [structure with N—CH$_3$, N$^+$—C$_2$H$_5$, ClO$_4^-$] | Pink to clear |
| IX. [structure with N-phenyl, N$^+$—C$_2$H$_5$, ClO$_4^-$] | Pink to clear |
| X. [structure with —CH=CH—, N-phenyl, N$^+$—C$_2$H$_5$] p-toluenesulfonate | Purple to yellow |
| XI. [structure with —CH=CH—, N-phenyl, N$^+$—C$_2$H$_5$] p-toluenesulfonate | Purple to yellow |

TABLE I-continued
Microbially Catalyzed Color Changes with Benzindole Dyes
| Dye | Visible Color Change |
|---|---|
| XII. 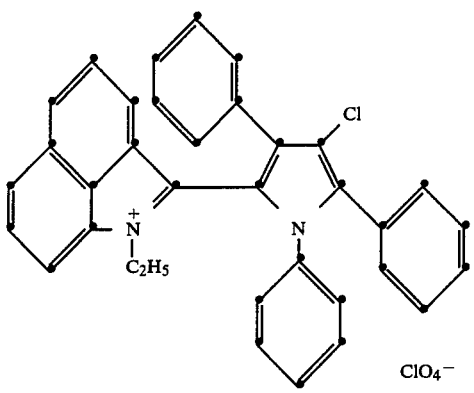 ClO$_4^-$ | Pink to colorless |
| XIII. 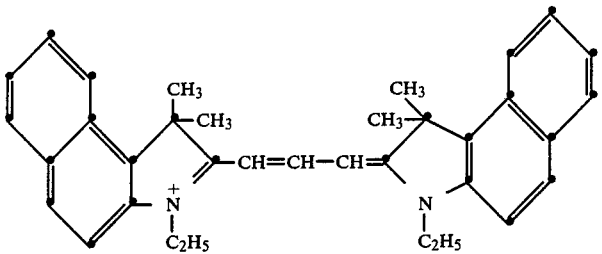 I$^-$ | No change |
| XIV. 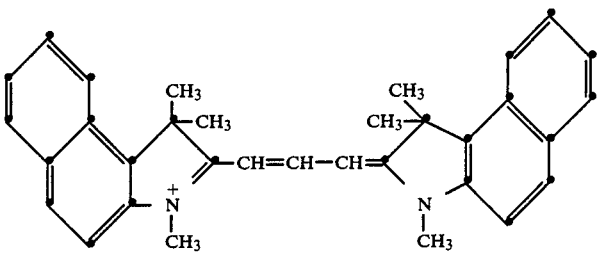 I$^-$ | No change |
| XV. 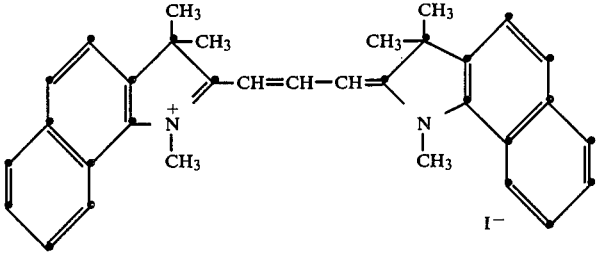 I$^-$ | No change |
| XVI. 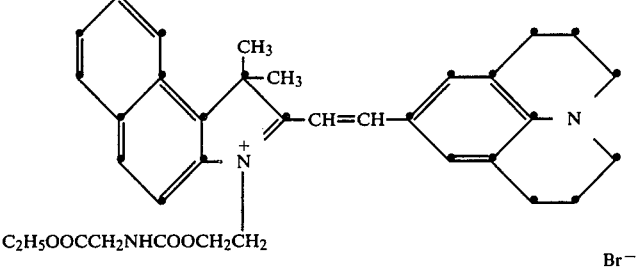 C$_2$H$_5$OOCCH$_2$NHCOOCH$_2$CH$_2$ Br$^-$ | No change |

TABLE I-continued

Microbially Catalyzed Color Changes with Benzindole Dyes

| Dye | Visible Color Change |
|---|---|
| XVII. [naphthalene-fused indolinium with N-CH$_2$CH$_2$OH, C(CH$_3$)$_2$-CH=CH- linked to julolidine], Br$^-$ | No change |
| XVIII. [naphthalene-fused indolinium with N-CH$_2$CH$_2$OCONHCH$_2$COOC$_2$H$_5$, C(CH$_3$)$_2$-CH=CH-C$_6$H$_4$-N(CH$_3$)$_2$], Br$^-$ | No change |
| XIX. [naphthalene-fused indolinium with N-C$_2$H$_5$, C(CH$_3$)$_2$-CH=CH-C$_6$H$_4$-N(CH$_3$)$_2$], ClO$_4^-$ | No change |
| XX. [naphthalene-fused indolinium with N-C$_2$H$_5$, C(CH$_3$)$_2$-CH=CH-C$_6$H$_4$-N(CH$_3$)$_2$], I$^-$ | No change |
| XXI. [naphthalene-fused indolinium with N-CH$_2$CH$_2$OH, C(CH$_3$)$_2$-CH=CH-C$_6$H$_4$-N(CH$_3$)$_2$], Br$^-$ | No change |
| XXII. [naphthalene-fused indolinium with N-(CH$_2$)$_3$OH, C(CH$_3$)$_2$-CH=CH-C$_6$H$_4$-N(CH$_3$)$_2$], Br$^-$ | No change |

TABLE I-continued

Microbially Catalyzed Color Changes with Benzindole Dyes

| Dye | Visible Color Change |
|---|---|
| XXIII. [naphthyl-C(CH₃)₂-indolium (N-CH₂CH₂OH)]−CH=CH−[C₆H₄−OCH₃]  Br⁻ | Orange to colorless (16 hrs.) |
| XXIV. [naphthyl-C(CH₃)₂-indolium (N-CH₂CH₂OCONHCH₂COOC₂H₅)]−CH=CH−CH=CH−[C₆H₄−N(CH₃)₂]  I⁻ | Blue to colorless (16 hrs.) |
| XXV. [naphthyl-C(CH₃)₂-indolium (N-C₂H₅)]−CH=CH−CH=CH−[C₆H₄−N(CH₃)₂]  I⁻ | Blue to colorless (16 hrs.) |
| XXVI. [naphthyl-C(CH₃)₂-indolium (N-CH₂CH₂OH)]−CH=CH−CH=CH−[C₆H₄−N(CH₃)₂]  Br⁻ | Blue to colorless (16 hrs.) |
| XXVII. [naphthyl-C(CH₃)₂-indolium (N-(CH₂)₃OH)]−CH=CH−CH=CH−[C₆H₄−N(CH₃)₂]  Br⁻ | Blue to colorless (16 hrs.) |
| XXVIII. [naphthyl-C(CH₃)₂-indolium (N-CH₃)]−CH=CH−[C₆H₄−N(CH₃)₂]  I⁻ | No change |

TABLE I-continued
Microbially Catalyzed Color Changes with Benzindole Dyes
| Dye | Visible Color Change |
|---|---|
| XXIX. 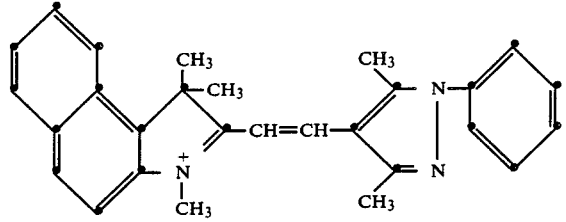 I⁻ | No change |
| XXX. 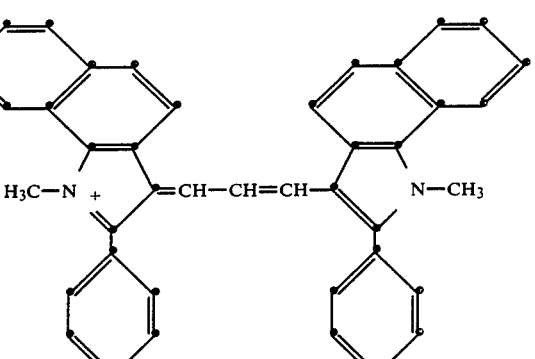 Br⁻ | No change |
| XXXI. 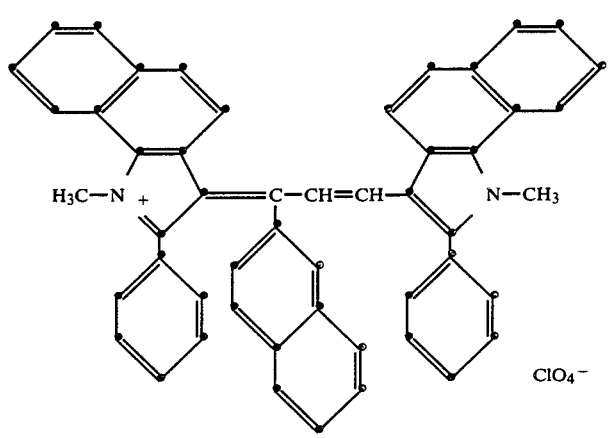 ClO₄⁻ | Yellow to colorless (16 hrs.) |
| XXXII. 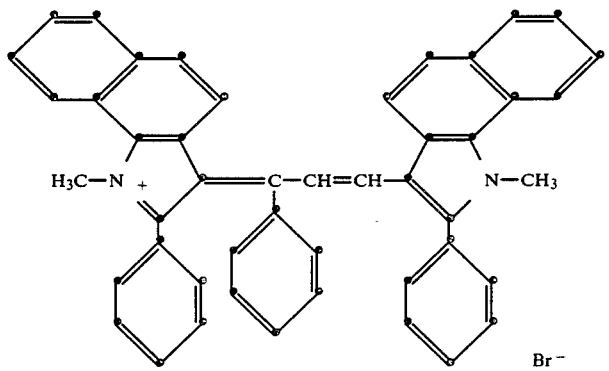 Br⁻ | Green to colorless (16 hrs.) |

TABLE I-continued

Microbially Catalyzed Color Changes with Benzindole Dyes

| Dye | Visible Color Change |
|---|---|
| XXXIII. (structure: naphthalene–benzindolium with CH=CH linkage to N-methyl-6-nitrobenzothiazole; p-toluenesulfonate) | Yellow to colorless (16 hrs.) |
| XXXIV. (structure: naphthalene–benzindolium with CH=CH linkage to 1,3-diethyl-4,5-dimethyl-imidazolium fused with phenyl; I$^-$) | Orange to colorless (16 hrs.) |
| XXXV. (structure: naphthalene–benzindolium with CH=CH linkage to 1,3-diphenyl-imidazolium with phenyl substituents) | Red to pink |
| XXXVI. (structure: 5,6-dichloro-1-(CH$_2$CH$_2$N(C$_2$H$_5$)$_2$)-3-ethyl-benzimidazolium with CH=CH—CH= linkage to 1,1,2-trimethyl-N-methyl-benzindole; I$^-$) | No change |

EXAMPLE 2

Color Changes Induced in a Preferred Dye Solution Using Urine Samples with and without a Significant Number of E. coli The effects of urine samples, with and without a significant number of a common urinary tract bacteria (*E. coli*), on the visible spectrum of a preferred dye, were compared using the following procedure: Two urine samples, (A) containing at least $10^5$ *E. coli*/mL, as determined by a local hospital and (B) normal having little bacteria, were collected and prepared as described above. Twenty-five microliters of a solution of benz[cd]indole dye I of Table I, prepared as above, was added to each tube. The contents of each tube were gently mixed and incubated for about 30 minutes at 37° C. in the dark, after which the visible spectrum of each tube was scanned from 300 nm to 700 nm. A control tube (C) prepared as described above was also scanned. A large decrease in the dye peak (600–620 nm) and a concomitant increase in the ultraviolet region of the spectrum was observed in the positive sample (A) as compared to the spectra of the normal urine sample (B) and the control dye solution (C).

EXAMPLE 3

Color Changes Induced in Dye Solutions Incubated with Pure Cultures of Microorganisms Often Encountered in Urinary Tract Infections The procedure of Example 1 was repeated with eight bacterial microorganisms often encountered in urinary tract infections (UTI) using dye I of Table I. The microorganisms tested were: (a) *E. coli*, (b) *S. epidermidis*, (c) *E. cloacae*, (d) *S. aureus*, (e) *S. marcescens*, (f) *K. pneumoniae*, (g) *P. aeruginosa*, and (h) *P. vulgaris*. After about 30 minutes of incubation at 37° C., a visual color change was noted in each tube containing a cell suspension.

EXAMPLE 4

Comparison of the Rapid Screening Method of the Present Invention with Standard Plate Culture Procedures The method of the present invention, utilized as a rapid screening procedure for detecting significant bacteriuria, was compared to results determined by a conventional screening procedure, i.e., the calibrated loop direct streak method.

Urine samples, obtained from local hospitals, were evaluated using both the loop method and the method of this invention. Of 96 urine samples tested, 18 were determined to be positive (i.e., contained 100,000 or more microorganisms/mL) based on the conventional calibrated loop method. Sixteen of these "positive" samples were considered to be positive by the method of the present invention. The two samples determined as "positive" by the calibrated loop method and "negative" by the method of this invention were obtained from patients receiving long-term antibiotic treatment. It is believed that the presence of antibiotics in the urine for an extended period of time may affect the physiological state of the bacterial cell and inhibit its reaction with the benzindole dye useful in the practice of this invention.

In addition to the 16 "positive" samples noted above, 7 additional samples showed "positive" results using the method of the present invention. These 7 samples, however, gave "negative" results using the calibrated loop method, although 5 of the 7 samples showed some bacterial growth on the calibrated loop streak plates, as shown in Table II hereinbelow. The "false positives" of the calibrated loop method may be attributable to additional bacterial growth or changes in the physiological state of the cell between tests or to contamination during transport. On the other hand, they could also be attributable to errors inherent in the standard calibrated loop procedure.

The overall results, however, indicate good correlation between the two methods and substantiate the use of the method of the present invention as a suitable rapid screening procedure.

TABLE II

| Plate Count Results of "False Positives" | |
|---|---|
| Microorganism | Number |
| *Proteus mirabilis* | 80,000 |
| *E. coli* | 60,000 |
| Mixed flora | 50,000 |
| *E. coli* | 30,000 |
| *Pseudomonas species* | 10,000 |

Two samples had no significant bacterial growth.

EXAMPLE 5

Multilayered Element for the Detection of Bacterial Activity Utilizing Benzindole Dyes An analytical element was prepared according to the following procedure:

A polyethylene film support was coated to provide a spreading/reagent layer comprised of: poly(vinyltoluene-co-p-t-butylstyrene-co-methacrylic acid) (61:37:2 wt. ratio) beads (17.2 g/m$^2$), poly(n-butylacrylate-co-styrene-co-2-acryl-amido-2-methylpropane, sulfonic acid) (50:40:10 wt. ratio) binder (4 wt.%, based on bead weight) and a drop of Tween ™ 80 surfactant (available from Atlas Chemical located in Wilmington, Del.). Prior to coating, the beads had been soaked in an excess of a methanolic solution of benz[cd]indole dye I of Table I ($10^{-3}$M), centrifuged and washed several times with phosphate buffer to remove nonadsorbed dye.

Cell suspensions of *E. coli* were prepared as described above.

Bacterial evaluation was made by placing a 2 cm$^2$ element sample into each of two test tubes, one tube containing 5 mL of the *E. coli* suspension and the other tube containing only 5 mL of phosphate buffer (control). Both tubes were incubated at 37° C. for 35 minutes. The element samples were then removed from the tubes, allowed to dry, and reflectance measurements were determined on each sample with a Zeiss DMC 26 spectrophotometer.

A higher reflectance density, measured between 600 and 650 nm, was obtained from the element sample exposed to the microorganism than from the control sample.

EXAMPLE 6

Effect of Anaerobic Incubation Conditions on Microorganism/Dye Reactions, Using a Multilayered Element A polyethylene terephthalate support was coated with a reagent layer comprising the benz[cd]indole dye I of Table I (17.2 g/m$^2$ of a $10^{-3}$M methanolic solution), poly(acrylamide-co-2-acetoacetoxyethyl methacrylate) (90:10 wt. ratio) and Zonyl ™ FSN surfactant (available from DuPont located in Wilmington, Del.) and a spreading layer like that described in Example 5 except without the dye.

A 1 cm² sample of the element was put into each of 4 rubber-stoppered vials. Nitrogen gas, saturated in water, was bubbled into the vials for 10 minutes by means of a 20-gauge canula. A 16-gauge needle served as the gas outlet.

Ten microliters of a suspension of *E. coli* cells was injected into 2 of the vials and the same amount of potassium phosphate buffer was injected into the remaining 2 vials designated to serve as controls. All vials were continuously purged with $N_2$ gas for 30 minutes. The element samples were then removed from their vials, air dried, and the reflectance density of each was measured at 620 nm. The two elements exposed to the *E. coli* exhibited higher reflectance densities compared to the controls, shown as follows:

| Vial | $D_R$ |
|---|---|
| E. coli | 1.85 |
| E. coli | 1.83 |
| Control | 1.50 |
| Control | 1.52 |

EXAMPLE 7

Comparison of Various Benzindole Dyes

This is a comparative example showing the absence of color change using selected benzindole dyes outside the scope of this invention. These dyes (XXXVII–XLVII) are listed in Table III below and are described in U.S. Pat. No. 4,232,121 (issued Nov. 4, 1980 to Gilman, Jr. et al). These dyes are compared to benz[cd]indole dye I of Table I which is within the scope of this invention.

The tests were performed by adding 5 mL of cell suspension containing *E. coli* to a test tube. After the optical density was adjusted to 1 at 620 nm, 100 μL of a $10^{-3}$M methanolic solution of each dye and 100 μL of 10% w/v glucose were added to the cell supsension. Control tubes without microorganisms were also prepared as described above. The contents of each tube were gently mixed and incubated for 4 hours at 37° C. Observations for any color change were made at 30 minutes, 1 hour after the beginning and at the end, of the incubation period. The results are listed in Table III below.

TABLE III

| | Dye | Visible Color Change |
|---|---|---|
| I. | 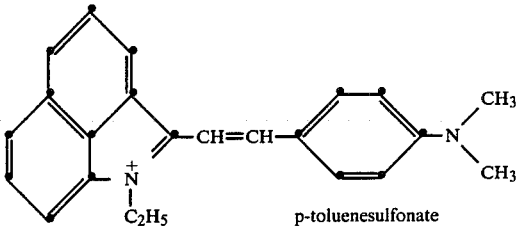 p-toluenesulfonate | Blue to yellow |
| XXXVII. | 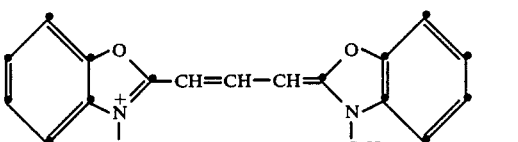 I⁻ | No change |
| XXXVIII. | 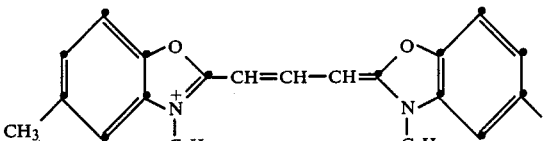 I⁻ | No change |
| XXXIX. | 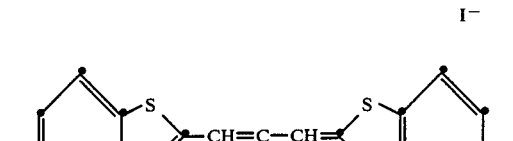 Br⁻ | No change |

TABLE III-continued

| Dye | Visible Color Change |
|---|---|
| XL. | Insoluble; precipitated |
| XLI. | No change |
| XLII. p-toluenesulfonate | No change |
| XLIII. p-toluenesulfonate | Insoluble; precipitated |
| XLIV. perchlorate | No change |
| XLV. p-toluenesulfonate | No change |

TABLE III-continued

| Dye | Visible Color Change |
|---|---|
| XLVI. 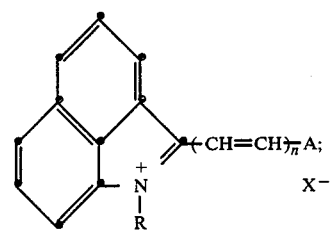 | No change |
| XLVII. 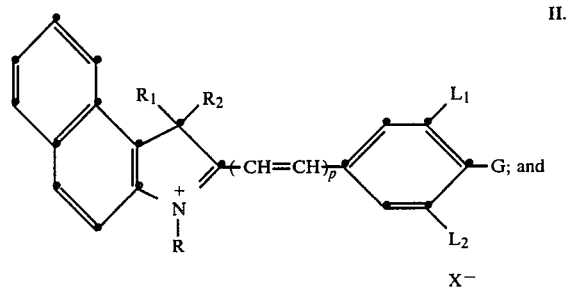 | No change |

The invention has been described in detail with particular reference to preferred embodiments thereof, but it will be understood that variations and modifications can be effected within the spirit and scope of the invention.

We claim:

1. A composition for the detection of a bacterial microorganism, said composition comprising a metabolizable substrate and a benzindole dye selected from the group consisting of benz[cd]indole dyes, benz[e]indole dyes and benzy[g]indole dyes, provided said dye undergoes a detectable color change when incubated at 37° C. in admixture with an aqueous suspension of said bacterial microorganism.

2. The composition of claim 1 wherein said benzindole dye has a structural formula selected from the group consisting of:

I.

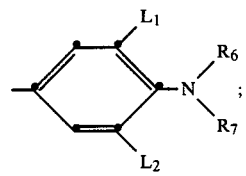

II.

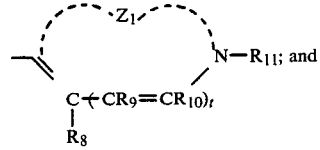

III.

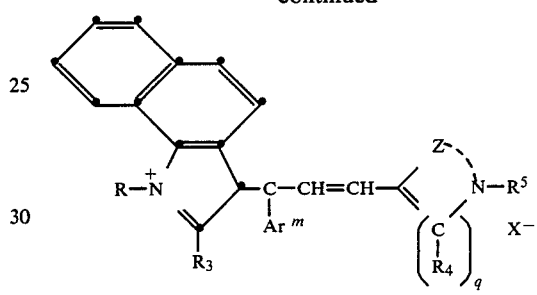

wherein:

A is selected from the group consisting of:

R, $R_4$, $R_5$ and $R_{11}$ are independently hydrogen, alkyl, aryl, alkaryl, aralkyl or cycloalkyl;

$R_1$ and $R_2$ are independently hydrogen or lower alkyl, or taken together complete a 5- to 6-membered carbocyclic ring;

$R_3$ is aryl;

$R_6$ and $R_7$ are independently hydrogen alkyl, cycloalkyl or aryl, or taken together complete a 4- to 20-membered heterocyclic group;

$R_8$, $R_9$ and $R_{10}$ are independently hydrogen, halo, alkyl, aryl, alkaryl, aralkyl or cycloalkyl;

G is —$OR_{12}$ or

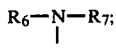

$R_{12}$ is lower alkyl;
$L_1$ and $L_2$ are independently hydrogen, or $L_1$ represents atoms taken with $R_6$ to complete a 5- or 6-membered ring or $L_2$ represents atoms taken with $R_7$ to complete a 5- or 6-membered ring;
Ar is aryl;
m and q are independently 0 or 1;
n is 0, 1, 2 or 3;
p is 1, 2 or 3, except when G is

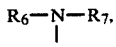

p is 2 or 3;
t is 0, 1 or 2;
s is 0, 1 or 2, except when n is 1, s is 1 or 2;
Z represents the carbon, selenium, sulfur or nitrogen atoms needed to complete a heterocyclic group;
$Z_1$ and $Z_2$ independently represent a single bond or the carbon, selenium, sulfur or nitrogen atoms needed to complete a heterocyclic group; and $X^-$ is a monovalent anion.
3. The composition of claim 2 wherein:

A is 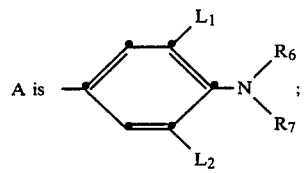 ;

R is hydrogen or lower alkyl;
G is

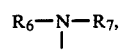

$R_1$ and $R_2$ are independently hydrogen or lower alkyl;
$R_4$ and $R_5$ are independently hydrogen or alkyl;
n is at least 1; and
p is 2 or 3.
4. The composition of claim 2 wherein said benzindole dye is selected from the group consisting of:

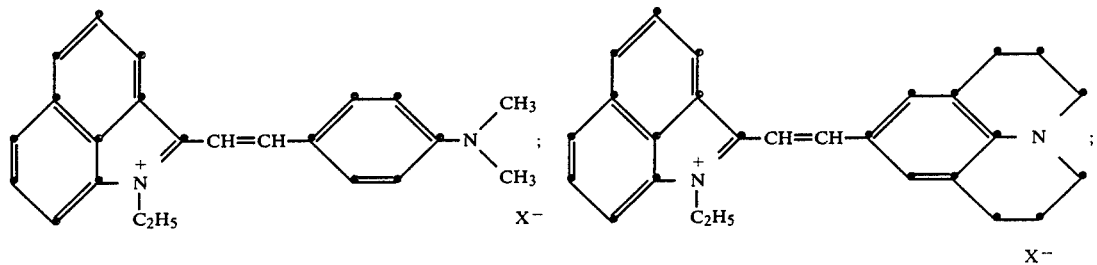

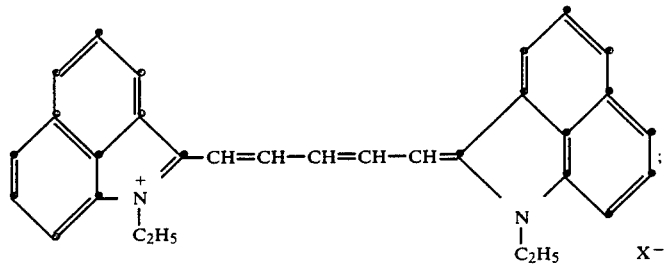

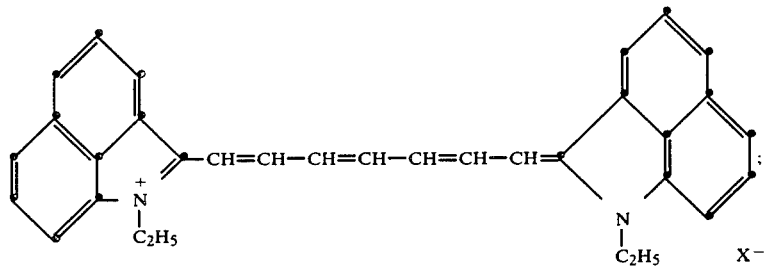

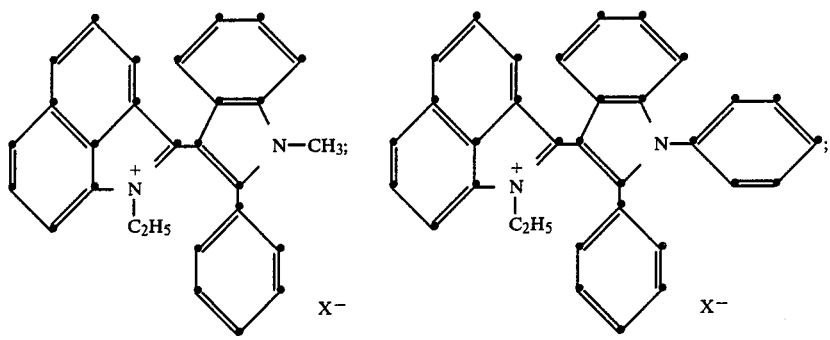
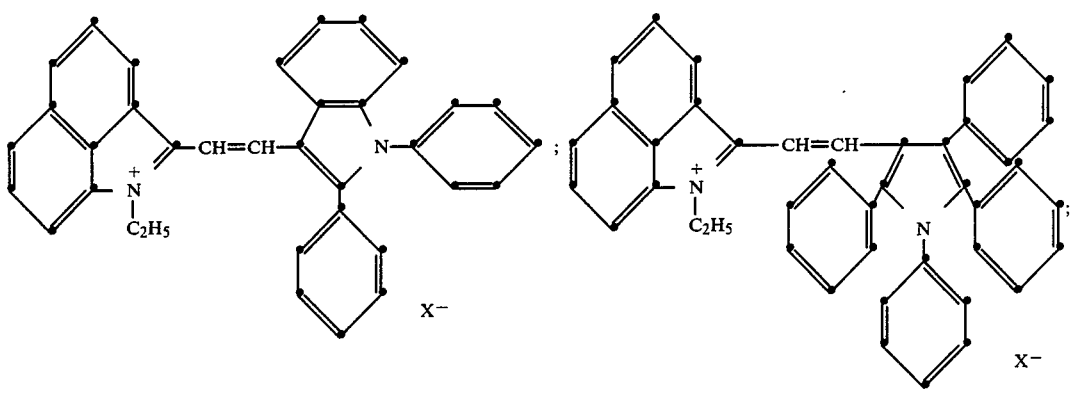
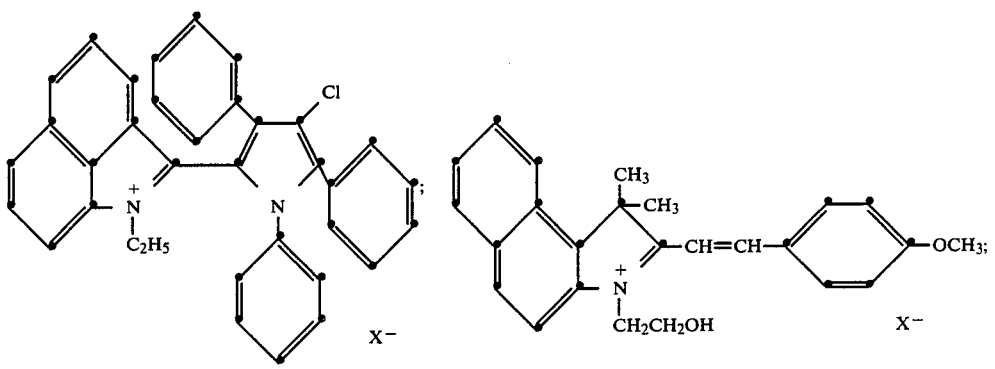
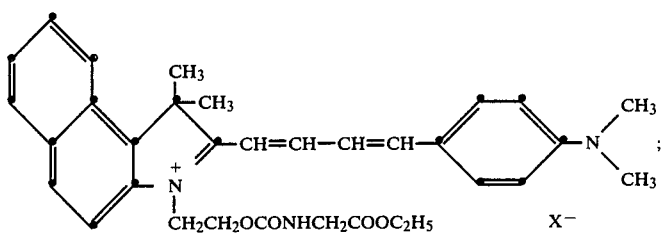
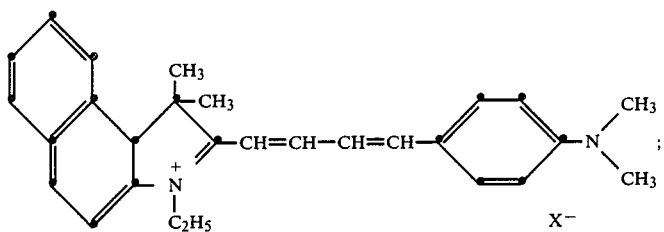

-continued
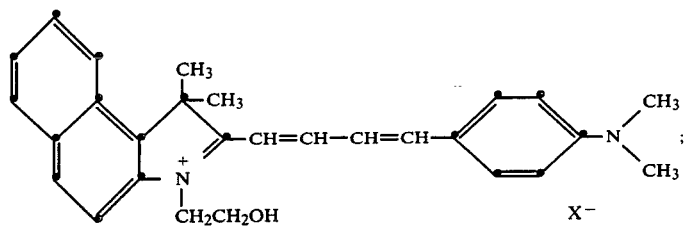
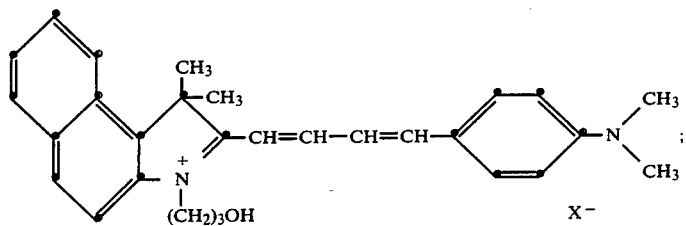
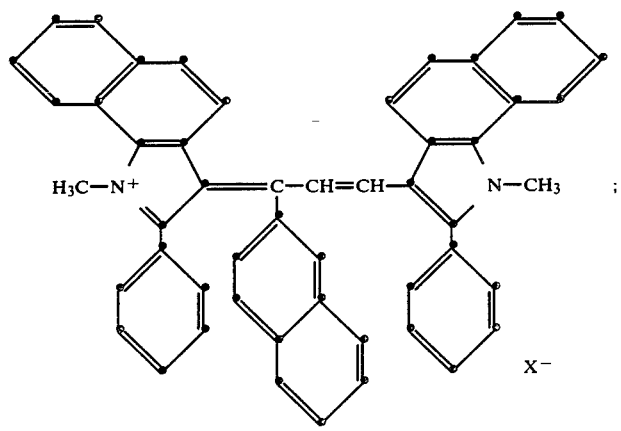
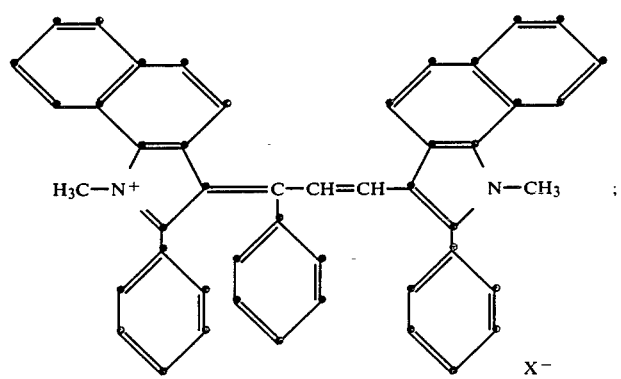

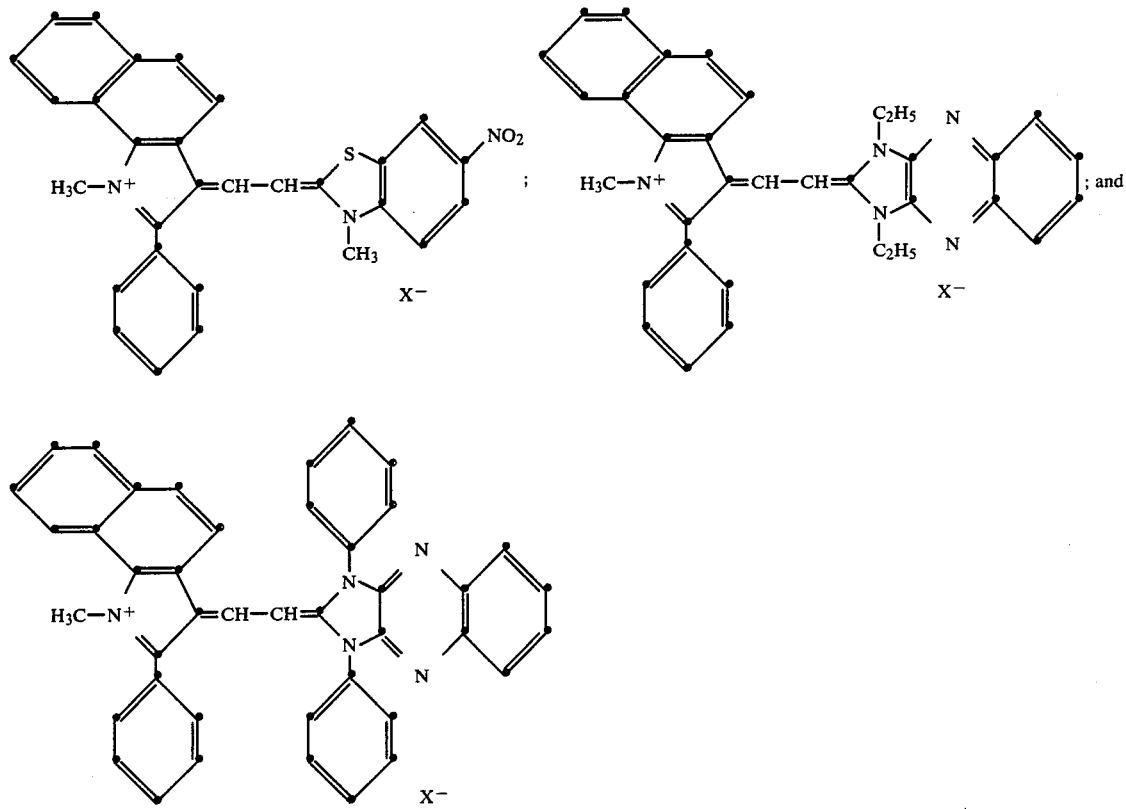

wherein X⁻ is a monovalent anion.

5. The composition of claim 3 wherein said benzindole dye is

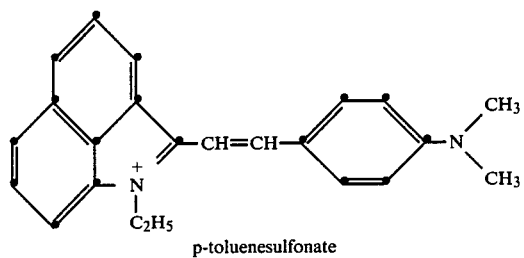

p-toluenesulfonate

6. The composition of claim 2 wherein X⁻ is p-toluenesulfonate, halide, acetate or perchlorate.

7. The composition of claim 1 wherein said benzindole dye is present in a concentration of up to about $10^{-1}$M.

8. The composition of claim 1 wherein said metabolizable substrate is a sugar, starch, salt of a carboxylic acid or glycol.

9. The composition of claim 8 wherein said metabolizable substrate is glucose.

10. An analytical element for detecting a bacterial microorganism, said element comprising an absorbent material containing a benzindole dye selected from the group consisting of benz[cd]indole dyes, benz[e]indole dyes and benzy[g]indole dyes, provided said dye undergoes a detectable color change when incubated at 37° C. in admixture with an aqueous suspension of said bacterial microorganism.

11. The element of claim 10 wherein said benzindole dye has a structural formula selected from the group consisting of:

I.

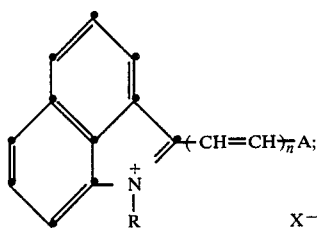

II.

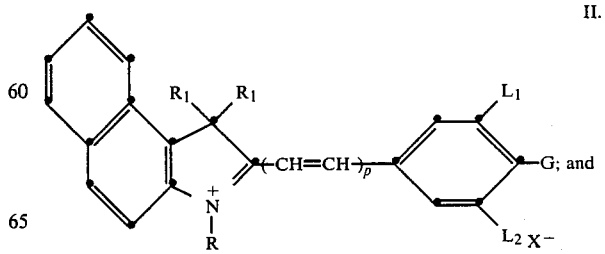

-continued

III.

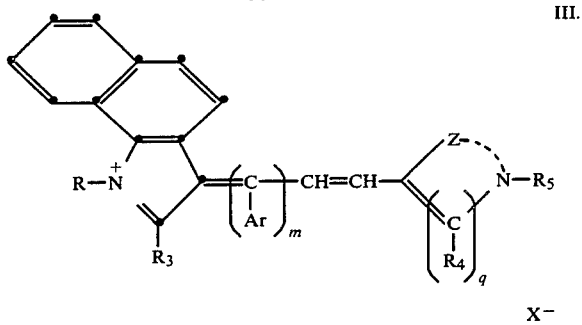

wherein:

A is selected from the group consisting of:

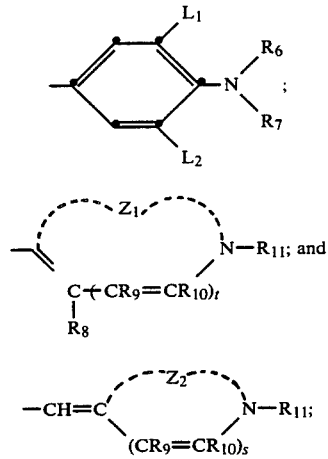

R, R$_4$, R$_5$ and R$_{11}$ are independently hydrogen, alkyl, aryl, alkaryl, aralkyl or cycloalkyl;

R$_1$ and R$_2$ are independently hydrogen or lower alkyl, or taken together complete a 5- to 6-membered carbocyclic ring;

R$_3$ is aryl;

R$_6$ and R$_7$ are independently hydrogen, alkyl, cycloalkyl or aryl, or taken together complete a 4- to 20-membered heterocyclic group;

R$_8$, R$_9$ and R$_{10}$ are independently hydrogen, halo, alkyl, aryl, alkaryl, aralkyl or cycloalkyl;

G is —OR$_{12}$ or

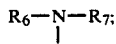

R$_{12}$ is lower alkyl;

L$_1$ and L$_2$ are independently hydrogen, or L$_1$ represents atoms taken with R$_6$ to complete a 5- or 6-membered ring or L$_2$ represents atoms taken with R$_7$ to complete a 5- or 6-membered ring;

Ar is aryl;

m and q are independently 0 or 1;

n is 0, 1, 2 or 3;

p is 1, 2 or 3, except when G is

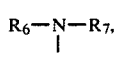

p is 2 or 3;

t is 0, 1 or 2;

s is 0, 1 or 2, except when n is 1, s is 1 or 2;

Z represents the carbon, selenium, sulfur or nitrogen atoms needed to complete a heterocyclic group;

Z$_1$ and Z$_2$ independently represent a single bond or the carbon, selenium, sulfur or nitrogen atoms needed to complete a heterocyclic group; and X$^-$ is a monovalent anion.

12. The element of claim 10 comprising a spreading-/reagent zone containing acid benzindole dye.

13. The element of claim 12 wherein said spreading-/reagent zone comprises polymeric beads of poly(vinyltoluene-co-p-t-butylstyrene-co-methacrylic acid).

14. The element of claim 10 wherein said benzindole dye is present at a coverage of from about $10^{-3}$ to about 1 g/m$^2$.

15. The element of claim 10 comprising a metabolizable substrate.

16. An analytical element for detecting a bacterial microorganism, said element including a support having thereon and, in fluid contact, reagent and spreading zones, said reagent zone containing a benzindole dye selected from the group consisting of benz[cd]indole dyes, benz[e]indole dyes and benz[g]indole dyes, provided that said dye undergoes a detectable color change when incubated at 37° C. in admixture with an aqueous suspension of said bacterial microorganism.

17. The element of claim 16 wherein said reagent zone is a layer adjacent said support, and said spreading zone is a layer comprising polymeric beads of poly(-vinyltoluene-co-p-t-butylstyrene-co-methacrylic acid).

18. A method for the detection of a bacterial microorganism comprising bringing a specimen sample suspected of containing a bacterial microorganism for analysis into contact with a benzindole dye selected from the group consisting of benz[cd]indole dyes, benz[e]indole dyes and benz[g]indole dyes, provided that said dye undergoes a detectable color change when incubated at 37° C. in admixture with an aqueous suspension of said bacterial microorganism and observing said color change which indicates the presence of said microorganism.

19. The method of claim 18 wherein said benzindole dye has a structural formula selected from the group consisting of:

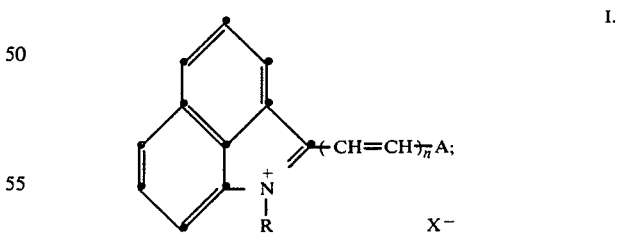

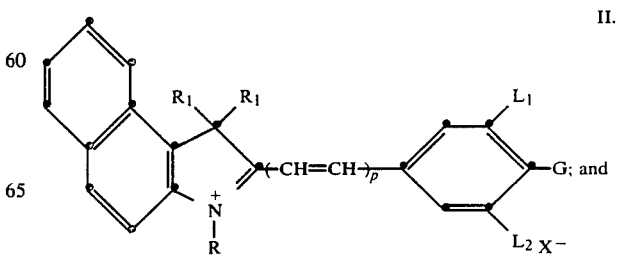

-continued

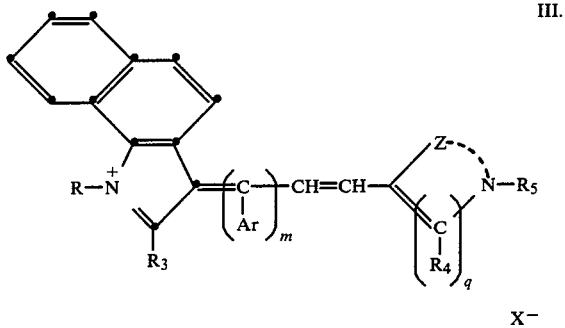

wherein:
A is selected from the group consisting of:

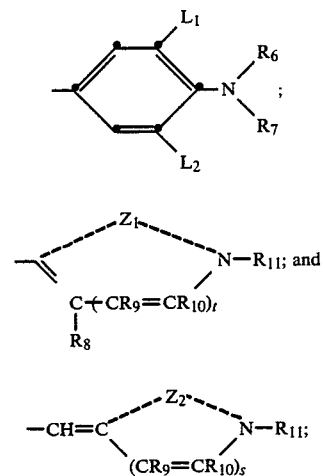

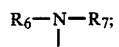

R, R$_4$, R$_5$ and R$_{11}$ are independently hydrogen, alkyl, aryl, alkaryl, aralkyl or cycloalkyl;

R$_1$ and R$_2$ are independently hydrogen or lower alkyl, or taken together complete a 5- to 6-membered carbocyclic ring;

R$_3$ is aryl;

R$_6$ and R$_7$ are independently hydrogen, alkyl, cycloalkyl or aryl, or taken together complete a 4- to 20-membered heterocyclic group;

R$_8$, R$_9$ and R$_{10}$ are independently hydrogen, halo, alkyl, aryl, alkaryl, aralkyl or cycloalkyl;

G is —OR$_{12}$ or

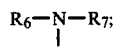

R$_{12}$ is lower alkyl;

L$_1$ and L$_2$ are independently hydrogen, or L$_1$ represents atoms taken with R$_6$ to complete a 5- to 6-membered ring or L$_2$ represents atoms taken with R$_7$ to each complete a 5- or 6-membered ring;

Ar is aryl;

m and q are independently 0 or 1;

n is 0, 1, 2 or 3;

p is 1, 2 or 3 except when G is

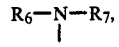

p is 2 or 3;

t is 0, 1 or 2;

s is 0, 1 or 2, except when n is 1, s is 1 or 2;

Z represents the carbon, selenium, sulfur or nitrogen atoms needed to complete a heterocyclic group;

Z$_1$ and Z$_2$ independently represent a single bond or the carbon, selenium, sulfur or nitrogen atoms needed to complete a heterocyclic group; and X$^-$ is a monovalent anion.

20. The method of claim 18 wherein:

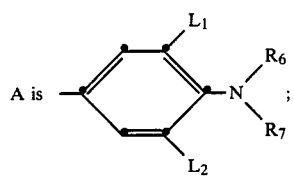

R is hydrogen or lower alkyl;
G is

R$_6$—N—R$_7$;

R$_1$ and R$_2$ are independently hydrogen or lower alkyl;

R$_4$ and R$_5$ are independently hydrogen or alkyl;

p is 2 or 3;

n is at least 1; and

X$^-$ is p-toluenesulfonate, halide, acetate or perchlorate.

21. The method of claim 18 wherein said incubation occurs in the presence of a metabolizable substrate.

22. The method of claim 21 wherein said metabolizable substrate is glucose.

23. A method for the detection of a bacterial microorganism, said method comprising contacting a urine sample suspected of containing a bacterial with a benzindole dye selected from the group consisting of benz[cd]indole dyes, benz[e]indole dyes and benzy[g]indole dyes provided that said dye undergoes a detectable color change when incubated at 37° C. in admixture with an aqueous suspension of said bacterial microorganism and observing said color change which indicates the presence of said microorganism.

24. A method for the detection of a bacterial microorganism in a specimen sample, said method comprising bringing said sample suspected of containing a bacterial microorganism into contact with an analytical element including a support and a spreading/reagent zone containing a benzindole dye selected from the group consisting of benz[cd]indole dyes, benz[e]indole dyes and benz[g]indole dyes, provided said dye undergoes a detectable color change when incubated at 37° C. in admixture with an aqueous suspension of said bacterial microorganism and observing said color change which indicates the presence of said microorganism.

25. The method of claim 24 wherein said specimen sample is spotted onto said spreading/reagent zone.

* * * * *

UNITED STATES PATENT AND TRADEMARK OFFICE
CERTIFICATE OF CORRECTION

PATENT NO. : 4,556,636
DATED : December 3, 1985
INVENTOR(S) : Robert T. Belly and Laurie J. Clements It is certified that error appears in the above-identified patent and that said Letters Patent are hereby corrected as shown below:

Column 4, lines 20-29, delete " 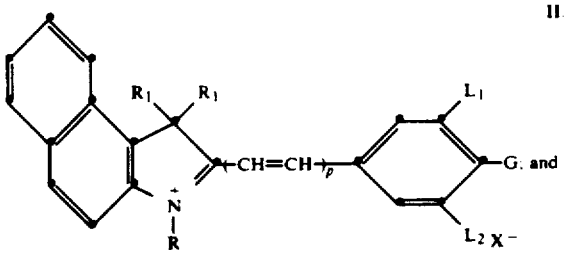 "

and substitute therefor

-- 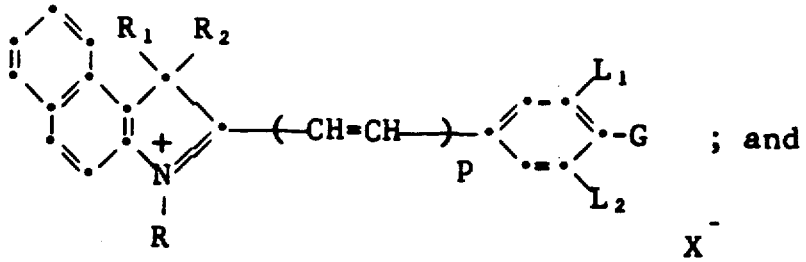 --;

UNITED STATES PATENT AND TRADEMARK OFFICE
CERTIFICATE OF CORRECTION

PATENT NO. : 4,556,636
DATED : December 3, 1985
INVENTOR(S) : Robert T. Belly and Laurie J. Clements It is certified that error appears in the above-identified patent and that said Letters Patent are hereby corrected as shown below:

Column 42, lines 56-65, delete " 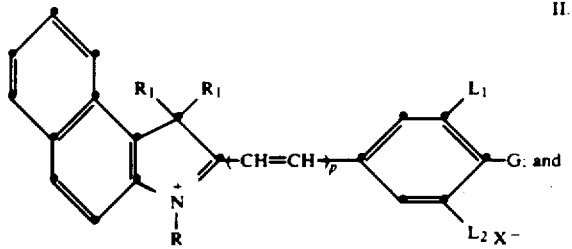 "

and substitute therefor

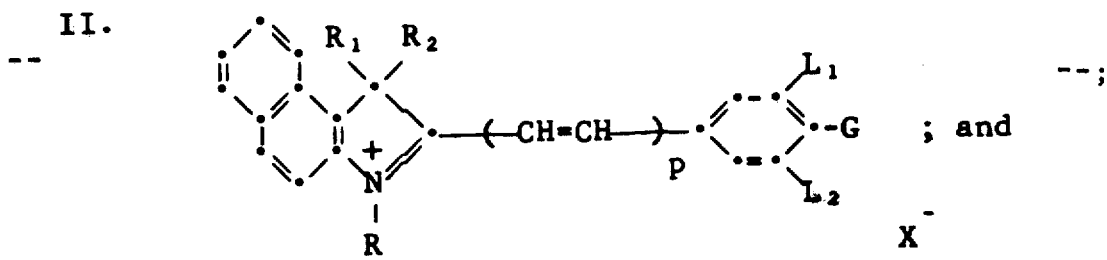

UNITED STATES PATENT AND TRADEMARK OFFICE
CERTIFICATE OF CORRECTION

PATENT NO. : 4,556,636
DATED : December 3, 1985
INVENTOR(S) : Robert T. Belly and Laurie J. Clements It is certified that error appears in the above-identified patent and that said Letters Patent are hereby corrected as shown below:

Column 44, lines 58-65, delete " 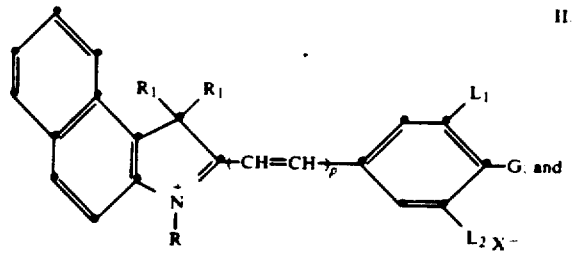 "

and substitute therefor

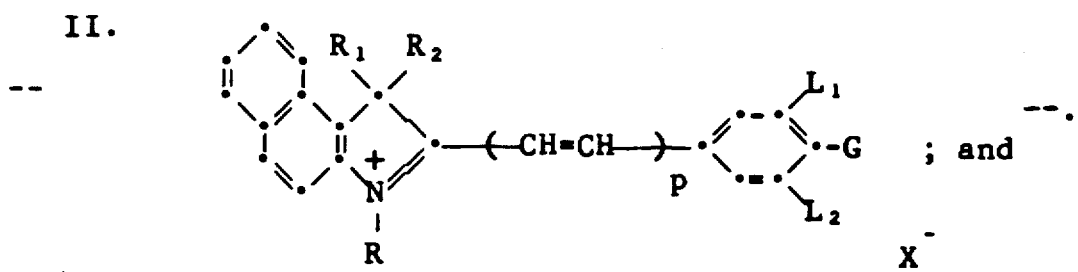

Signed and Sealed this

First Day of July 1986

[SEAL]

Attest:

DONALD J. QUIGG

Attesting Officer  Commissioner of Patents and Trademarks